United States Patent [19]

Oshikubo

[11] Patent Number: 5,021,217
[45] Date of Patent: Jun. 4, 1991

[54] MULTIPIPET
[75] Inventor: Yuju Oshikubo, Tokyo, Japan
[73] Assignee: Nichiryo Co., Ltd., Tokyo, Japan
[21] Appl. No.: 368,276
[22] Filed: Jun. 19, 1989
[30] Foreign Application Priority Data Dec. 20, 1988 [JP] Japan .................................. 63-321304

[51] Int. Cl.⁵ .......................... B01L 3/02; G01N 1/14
[52] U.S. Cl. .............................. 422/100; 73/864.13;
73/864.14; 73/864.17; 73/863.32
[58] Field of Search ..................... 422/100; 73/864.13,
73/864.14, 864.17, 863.32

[56] References Cited
U.S. PATENT DOCUMENTS 3,855,868 12/1974 Sudvaniemi ........................ 73/425.6
4,215,092 7/1980 Suovaniemi et al. ............. 73/863.32
4,335,621 6/1982 Tervamäki et al. .............. 73/863.32
4,444,062 4/1984 Bennett et al. ................... 73/863.32
4,599,220 7/1986 Yonkers et al. ...................... 422/100

FOREIGN PATENT DOCUMENTS

265028 2/1987 European Pat. Off. .

Primary Examiner—Robert J. Warden
Assistant Examiner—Theresa A. Trembley

[57] ABSTRACT

A multipipet designed to allow a plurality of cylinders to be supported by a supporting member in such a manner that each cylinder is individually oscillatable sideward relative to said supporting member. A multipipet designed to allow a plurality of plungers and a plurality of cylinders to be accommodated in a single housing and a gripping body to be attached to said housing through thread engagement.

7 Claims, 8 Drawing Sheets

MULTIPIPET

INDUSTRIAL FIELD OF THE INVENTION

The present invention relates to a multipipet having, for example 8 or 12 channels, which is so designed that the operation of assembling the same is facilitated and the working efficiency is improved.

BACKGROUND OF THE INVENTION

In one example of a conventional multipipet, a plurality of plungers are fixedly attached to a common supporting body at a predetermined pitch and a plurality of cylinders are also fixedly attached to another common supporting body at a predetermined pitch. In operation, the plungers are simultaneously and fittingly advanced in the respective cylinders against the force of springs. The plungers are then returned to suck predetermined amounts of liquid into the cylinders and then moved downward again to discharge the predetermined amounts of liquid from the cylinders.

The above-described arrangement suffers, however, from the following disadvantages. Since the pitch of the plungers and that of the cylinders are fixed, if there is any difference between the pitch of the plungers and that of the cylinders, this pitch error cannot be tolerated and the plungers are likely to be rubbed locally against the side walls of the cylinders to an extent corresponding to the degree of the dimensional error. In such a case, the reciprocating motion of the plungers cannot be effected smoothly, which interferes with the operation and lowers the pipetting accuracy. This problem may be overcome by increasing the precision of assembly, but this would lead to a very high cost for assembling the multipipet.

According to another prior art (see for example, Japanese Patent Publication No. 35557/1977), a plurality of plungers are oscillatably attached to a common supporting body through respective springs so that any small pitch error between the plungers and the cylinders is absorbed by each individual plunger which oscillates in such a manner as to adjustably fit the corresponding cylinder, thereby enabling the plungers to reciprocate smoothly within the cylinders, and thus eliminating the above-described disadvantages.

However, the above-described prior art suffers from the following disadvantages since the cylinders are still fixedly attached to another common supporting body. More specifically, when the distal end portions of the cylinders of the multipipet are simultaneously and respectively inserted into a plurality of nozzle tips supported on a nozzle tip rack, if there is an error between the pitch of the cylinders and that of the nozzle tips, some of the nozzle tips cannot be tightly fitted onto the distal end portions of the corresponding cylinders. Accordingly, it is necessary to make a manual check to determine whether or not each individual nozzle tip has been tightly and properly fitted onto the corresponding cylinder and, if any nozzle tip has not been properly fitted, it must be manually forced so as to fit onto the cylinder in its proper position. Thus, the operation of this prior art has been troublesome.

OBJECT OF THE INVENTION

One object of the invention is to provide an improved multipipet which is so designed that a plurality of plungers are respectively and fittingly advanced in a plurality of cylinders by a manual operation against the force of a spring, the plungers then being returned to suck predetermined amounts of liquid into the cylinders and thereafter moved downward again to discharge the predetermined amounts of liquid from the cylinders, wherein the improvement is characterized in that the cylinders are supported by a supporting member in such a manner that each cylinder is individually oscillatable sideward relative to the supporting member.

Accordingly, (1) when the plungers are moved downward, any small pitch error between the plungers and the cylinders can be absorbed by the cylinders which are capable of individually oscillating sideward in conformity with the pitch of the plungers, thus enabling the plungers to be moved up and down smoothly, and (2) when the distal end portions of the cylinders are respectively inserted into a plurality of nozzle tips, any small pitch error between the cylinders and the nozzle tips can also be absorbed by the individual sideward oscillation of the cylinders that occurs in conformity with the pitch of the nozzle tips, thus enabling the nozzle tips to be speedily and reliably fitted onto the cylinders.

Another object of the invention is to provide an improved multipipet which is so designed that the plungers and the cylinders are accommodated in a single housing, and that a gripping body which accommodates a push button and an intermediate mechanism is attached to the housing through threaded engagement.

Accordingly, the gripping body and the housing can be readily assembled and disassembled with respect to each other.

Other objects and advantageous effects will be explained below.

PREFERRED EMBODIMENT

Referring to FIGS. 1 to 6, the 8-channel multipipet 1 comprises a gripping body 2 and a housing 3.

The gripping body 2, which is made of a resin material, includes a metallic push shaft 4 (having a push button 5) which extends therethrough in such a manner that the push shaft 4 is slidable vertically (but horizontally as viewed in FIGS. 1 to 3 and 5) and biased upward by the force of a spring (not shown).

The housing 3, which is made of a resin material, accommodates a plunger unit 6 and a cylinder unit 7. In the plunger unit 6, eight metallic plungers 9 which are disposed at a predetermined pitch are screwed into the lower side of a metallic common bar 8 which acts as a common supporting member and one metallic shaft 10 is screwed into the upper side of the common bar 8. The plunger unit 6 is accommodated within the housing 3 in such a manner that the plunger unit 6 is vertically slidable. The shaft 10 projects upward from a bore provided in the ceiling portion of the housing 3. A bush 11 is fitted on the upper end portion of the shaft 10 and secured thereto by means of a setscrew 12. A spring 13 is disposed around the shaft 10 and retained at both ends thereof by the ceiling portion of the housing 3 and a spring retainer 14. Accordingly, the plunger unit 6 is biased upward by the force of the spring 13 and the common bar 8 is at an upper position where it abuts against a predetermined portion of the housing 3. An enlarged-size bore 15 is provided adjacent to the above bore of the ceiling portion of the housing 3. A nut 16 is accommodated in the enlarged-size bore 15 beforehand in such a manner that the outer peripheral portion of the nut 16 slightly projects from the outer surface of the housing 3 so as to enable the nut 16 to be manually and easily turned. The push shaft 4 has a small-diameter portion at the lower end thereof, which is fitted into a bush 21 in turn fitted into the bush 11. It should be noted here that, since the detailed arrangement inside the gripping body 2 is not particularly related to the present invention, description thereof is omitted (for further details, refer to Japanese patent application No. 234512/1987, "Variable Pipet" filed by the present applicant).

The cylinder unit 7 essentially comprises an upper cylinder holder 22, a lower cylinder holder 23 and eight cylinders 24 disposed therebetween.

The upper cylinder holder 22 is a rectangular plate made of a resin material. The upper cylinder holder 22 has a peripheral projection 22a (see FIGS. 6 and 7) projecting downward from the peripheral edge thereof and eight bores 22b (see FIG. 6) for receiving the eight plungers 9. The lower cylinder holder 23 has eight bores 23a (see FIG. 6) for receiving the respective cylinders 24. The upper and lower cylinder holders 22 and 23 are assembled together in opposing relation to each other with a plurality of sleeves 25 (see FIG. 5) interposed therebetween, and are rigidly secured together in one unit by means of long bolts (not shown) which extend through the respective sleeves 25.

Figure 6:
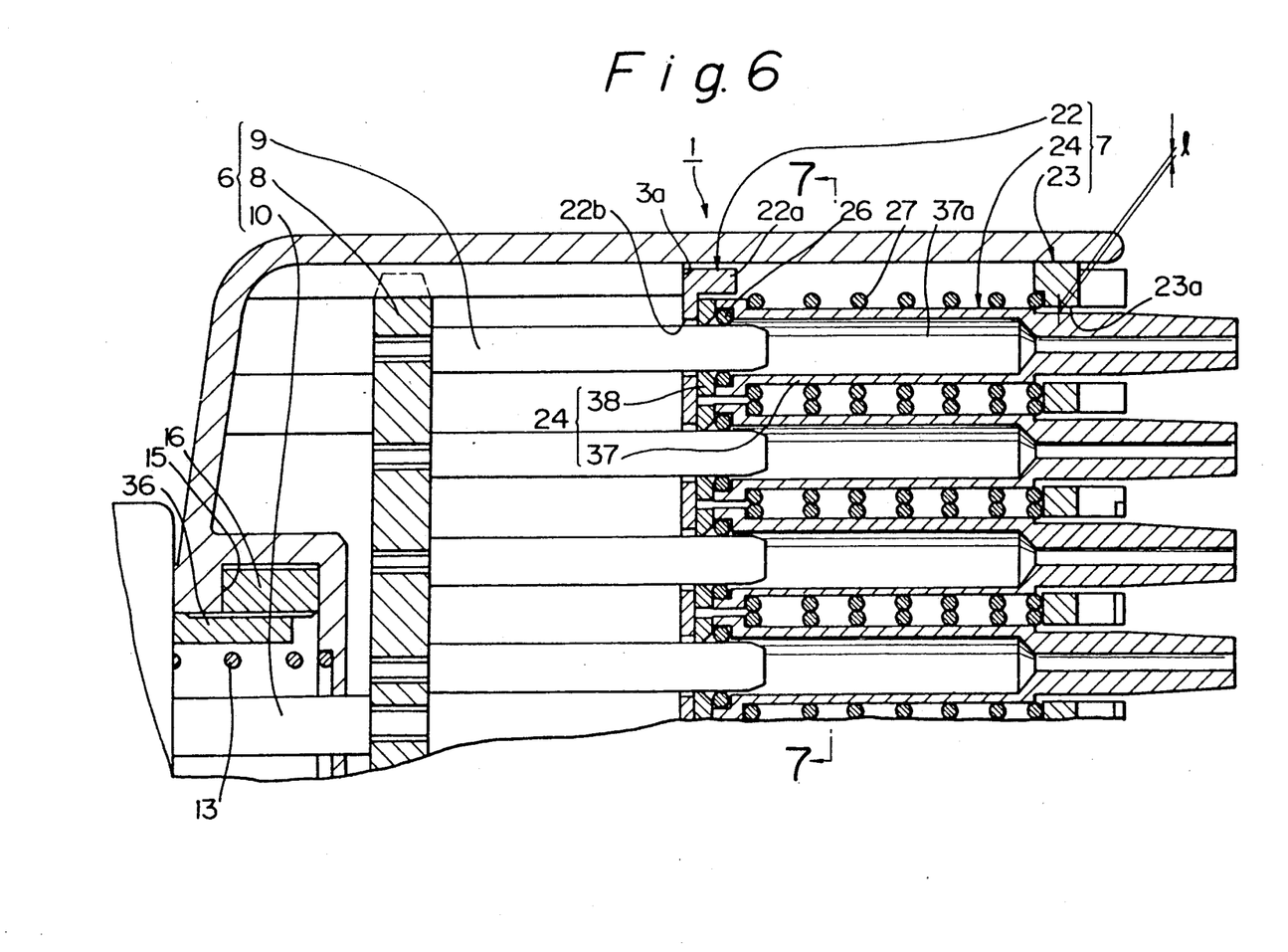
FIG. 6 is an enlarged longitudinal sectional front view of an essential part of the 8-channel multipipet.
Figure 7:
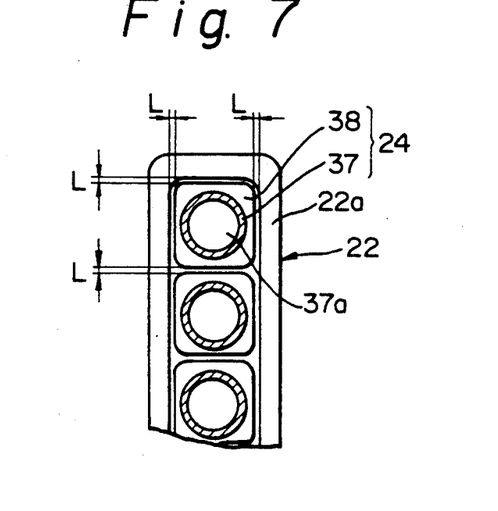
FIG. 7 is a sectional view taken along the line VII—VII of the cylinder unit shown in FIG. 6.

Each cylinder 24 comprises, as shown in FIG. 6, a circular cylinder body 37 (having a cylinder chamber 37a) made of a resin material, an O-ring retaining plate 38 (having a central bore) made of a resin material which is attached to the upper end of the cylinder body 37, and an O-ring 26 disposed within a step-shaped peripheral groove defined between the body 37 and the plate 38. Although the O-ring 26 is substantially completely accommodated within the step-shaped peripheral groove, when the cylinder 24 (including the O-ring retaining plate 38) is pressed against the upper cylinder holder 22 by the force of a spring 27 as described later, the O-ring 26 is forced to project radially inward by the slanted lower and inner peripheral surface of the central bore of the O-ring retaining plate 38, so that the O-ring 26 is pressed against the outer periphery of the corresponding plunger 9 to provide sealing. The cylinder 24 are assembled together in advance in such a manner that the square O-ring retaining plates 38 are accommodated within the peripheral projection 22a of the upper cylinder holder 22 and the lower portions of the cylinders 24 are movably fitted into the respective bores 23a in the lower cylinder holder 23, the cylinders 24 being disposed at a predetermined pitch which is the same as the pitch of the plungers 9. Further, each cylinder body 37 is biased upward by the force of a spring 27 provided on the outer periphery thereof, thus causing the O-ring retaining plate 38 to be pressed against the upper cylinder holder 22.

The cylinder unit 7 is accommodated within the housing 3 in such a manner as to abut against a step 3a (see FIG. 6) provided in the housing 3. Further, a plurality of long bolts (not shown) are inserted into the cylinder holders 22 and 23 from the lower side to the upper side thereof in the vicinity of the sleeves 25 and the projecting end portions of the bolts are screwed into predetermined portions of the housing 3, thereby rigidly securing the cylinder unit 7 to the housing 3. Each plunger 9 is fitted into the cylinder chamber 37a of the corresponding cylinder 24 by a predetermined amount through an O-ring 26 which provides sealing.

By virtue of the arrangement of the cylinder unit 7, the outer peripheral portion of the O-ring retaining plate 38 of each cylinder 24 has a radial gap L(e.g., L=0.3 mm) with respect to the peripheral projection 22a of the upper cylinder holder 22 and with respect to the next O-ring retaining plate 38. Further, the lower portion of each cylinder 24 has a radial gap l (e.g., l=0.2 mm; see FIG. 6) with respect to the associated bore 23a of the lower cylinder holder 23. Accordingly, each cylinder 24 is capable of individual sideward oscillating motion, that is, the upper end portion of the cylinder 24 is oscillatable (or rotatable) sideward by a distance corresponding to the gap L substantially around an oscillating (or rotating) center portion where the cylinder 24 is loosely fitted into the lower cylinder holder 23. Therefore, when the plungers 9 are inserted into the respective cylinders 24, any small pitch error therebetween is absorbed by the cylinders 24 which are individually oscillated sideward so as to adjustably fit the respective plungers 9, even though the pitch of the plungers 9 is fixed, thus enabling the plunger inserting operation to be conducted smoothly.

On the other hand, after the plungers 9 have already been inserted into the respective cylinders 24, each cylinder 24 is capable of individual sideward oscillating motion, that is, the lower portion of the cylinder 24 is oscillatable (or rotatable) sideward by a distance corresponding to the gap l substantially around an oscillating (or rotating) center portion where the cylinder 24 comes in contact with the plunger 9 through the O-ring 26. Accordingly, when the cylinders 24 are inserted into respective nozzle tips 44 as described later, the cylinders 24 are capable of individually oscillating sideward, thus enabling the nozzle tips 44 to be effectively and smoothly fitted onto the the respective cylinders 24.

Figure 1:
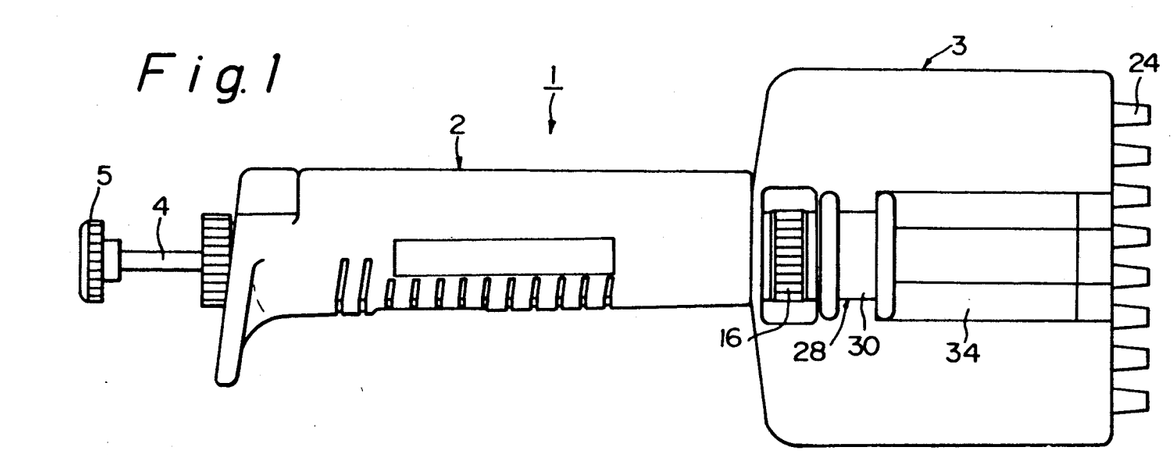
FIGS. 1 and 2 are front and side views, respectively, of an 8-channel multipipet which is one embodiment of the multipipet according to the present invention.
Figure 2:
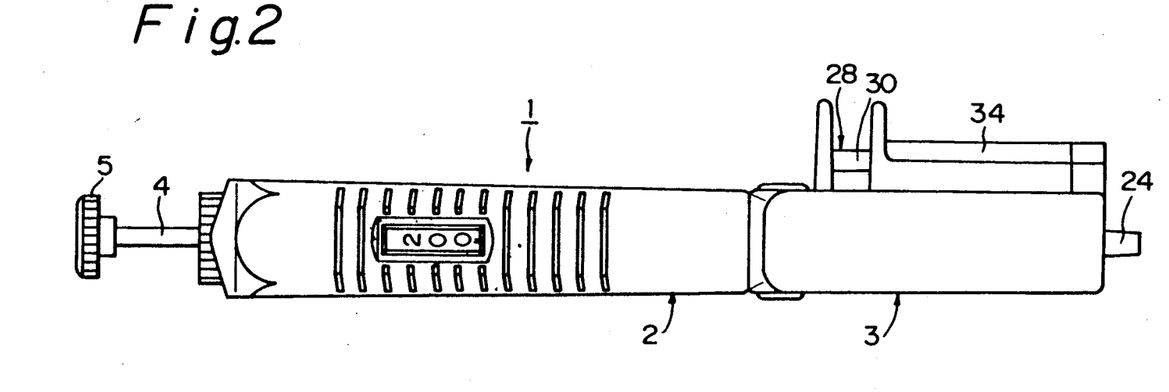
Figure 3:
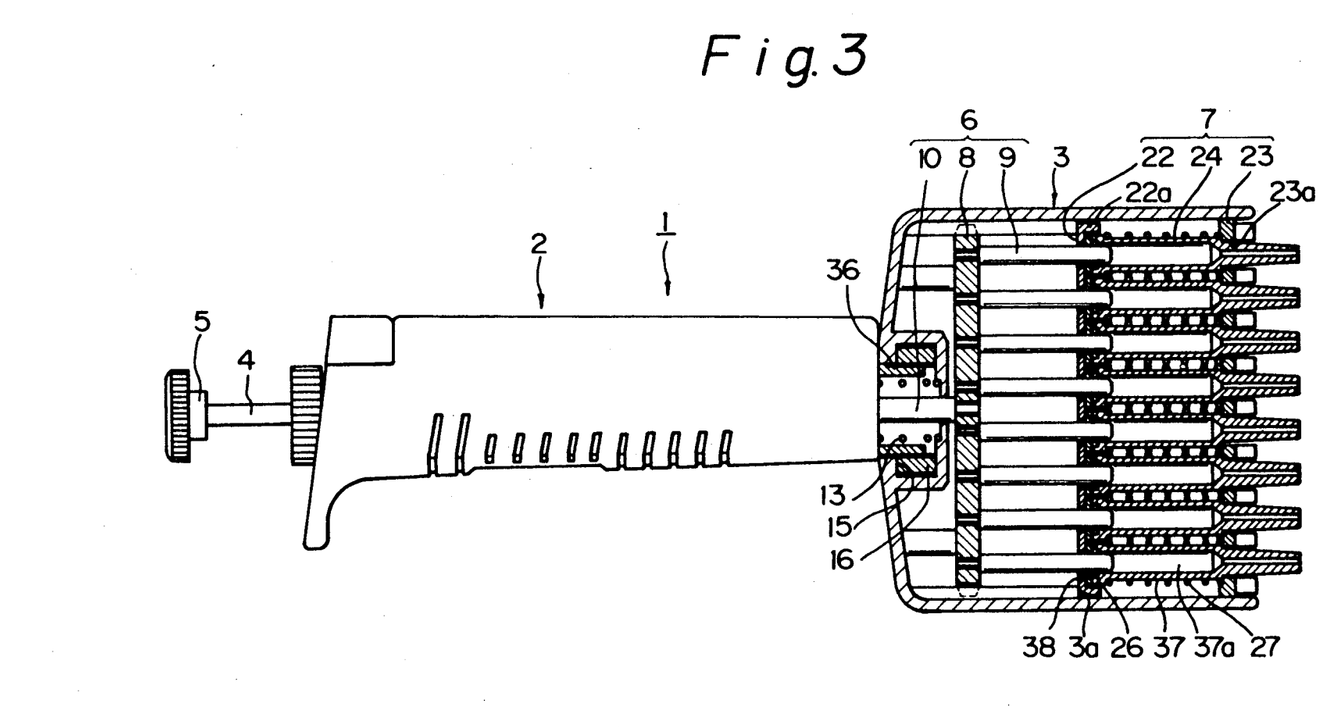
FIGS. 3 to 5 are a partially sectioned front view, a bottom view and a partially cutaway longitudinal sectional side view, respectively, of the 8-channel multipipet.
Figure 4:
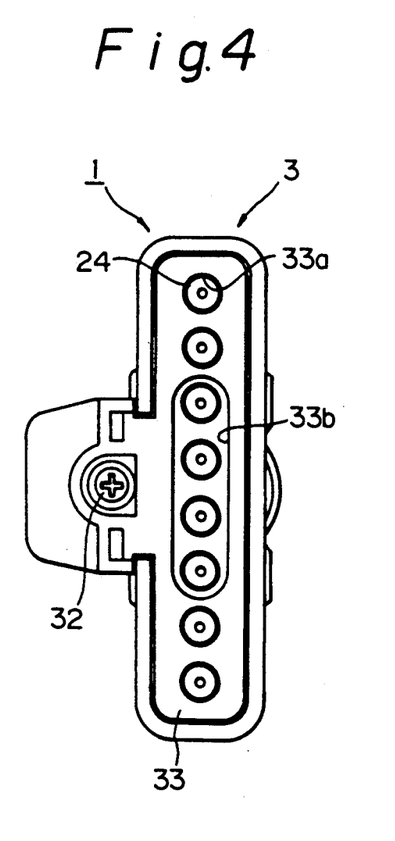
Figure 5:
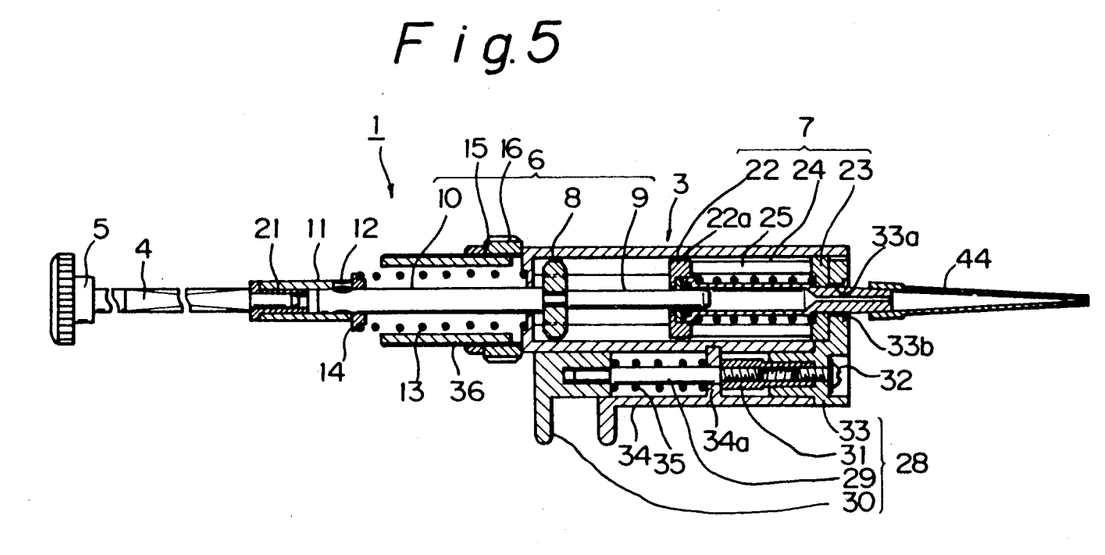

The reference numeral 28 denotes a nozzle tip ejector unit which comprises, as shown in FIG. 5, a metallic shaft 29 having threads respectively provided on the upper and lower end portions, a push button 30 made of a resin material which is rigidly screwed onto the upper end portion of the shaft 29, a sleeve 31 made of a metallic material which is screwed onto the lower end portion of the shaft 29, and a nozzle tip ejector 33 rigidly secured to the lower portion of the sleeve 31 by means of a screw 32. The ejector 33 is, as shown in FIG. 4, a rectangular plate made of a resin material which has eight bores 33 and a recess 33b which is formed in the bottom surface including the central four bores 33a.

The nozzle tip ejector unit 28 is accommodated within a side housing 34 provided on one side of the housing 3 with the metallic shaft 29 extending through a wall portion 34a of the housing 34. The nozzle tip ejector unit 28 is biased upward by the action of a spring 35 so that the sleeve 31 abuts against the wall portion 34a. At this time, the ejector 33 comes close to the lower side of the cylinder unit 7, and the lower end portion of each cylinder 24 projects downward through the corresponding bore 33a.

To assemble the gripping body 2 and the housing 3, a screw sleeve 36 which has previously been rigidly screwed to the lower end of the gripping body 2 such as to project downwardly is inserted into the central bore of the housing 3 and screwed into the nut 16 disposed within the enlarged-size bore 15 until the lower end (see FIGS. 1 to 3) of the gripping body 2 is pressed against the upper end of the housing 3. After the gripping body 2 has been rotated to a desired angular position relative to the housing 3, the nut 16 is turned manually to be tightened, thus enabling the gripping body 2 to be firmly secured to the housing 3.

With the above-described arrangement, the angle of the gripping body 2 relative to the housing 3 can be readily varied simply by loosening the nut 16, rotating the gripping body 2 relative to the housing 3 to adjust the relative angle and then re-tightening the nut 16. Thus, the angle adjusting operation is facilitated. The gripping body 2 can also be readily disassembled by reversing the procedure carried out in the assembly operation. In addition, the arrangement of the assembly of the gripping body 2 and the housing 3 enables the body 2 to be used as a common member irrespective of the number of channels provided in the housing 3, which is a very convenient feature. Further, since the gripping body 2 can be removed easily, when it is desired to inspect the plunger unit 6 in a situation where samples sucked into the cylinders 24 have undesirably passed beyond the O-rings 26 and reached the plungers 9, the plunger unit 6 can be readily disassembled by removing the body 2 and the bush 11 and then removing the cylinder unit 7. Thus, since the gripping body 2 and the housing 3 can be readily assembled and disassembled, inspection operations of various kinds are facilitated.

Figure 8:
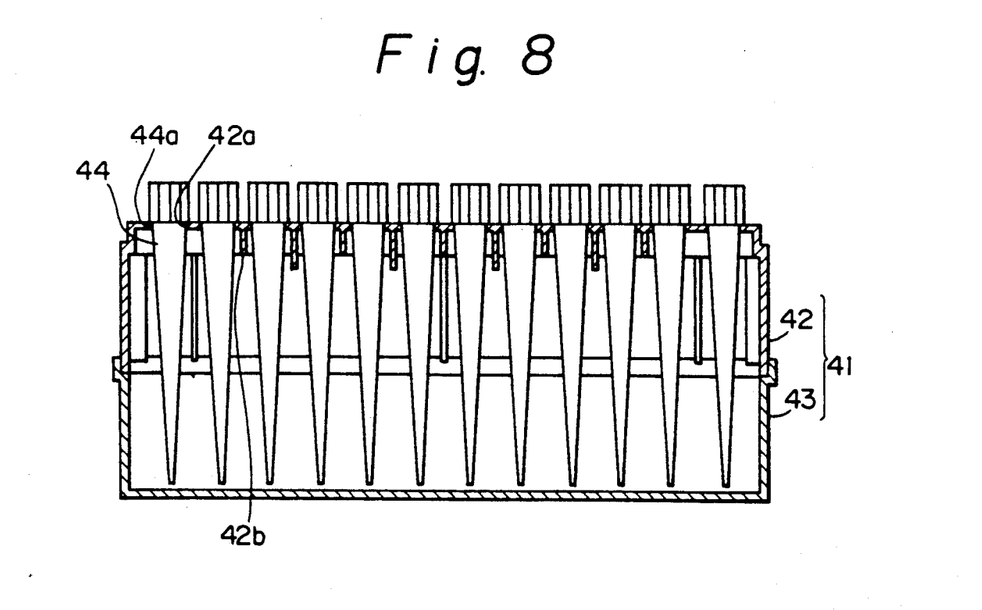
FIG. 8 is a vertical sectional view of nozzle tips supported in a nozzle tip rack.
Figure 9:
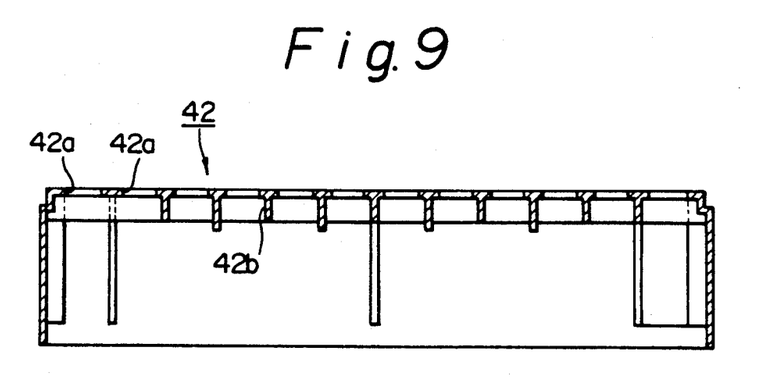
FIGS. 9 and 10 are a vertical sectional view and a bottom view, respectively, of the upper rack constituting the nozzle tip rack.
Figure 10:
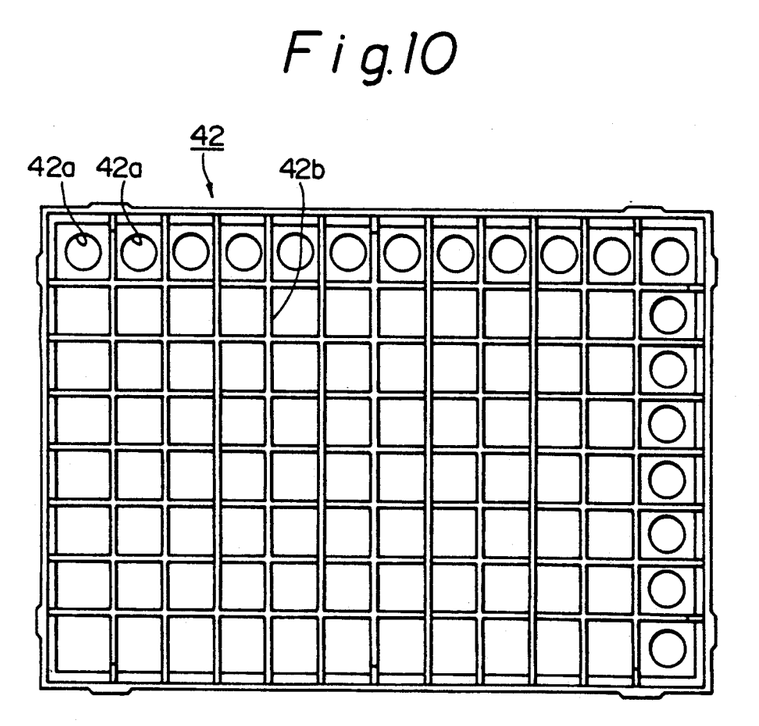

Referring to FIG. 8, the reference numeral 41 denotes a nozzle tip rack made of a resin material which is formed by assembling an upper box rack 42 and a lower box 43. As shown in FIGS. 9 and 10, the upper rack 42 is provided with, for example, a total of 96 bores 42a arranged in 8 vertical rows and 12 horizontal rows (the pitches of the bores 42a in both the vertical and horizontal rows being the same as the pitch of the cylinders 24), and reinforcing ribs 42b are provided on the inner surface of the upper rack 42 in such a manner as to partition off the bores 42a from each other. The reference numeral 44 denotes a total of 96 nozzle tips made of a resin material which are fitted into the respective bores 42a of the rack 41. Each nozzle tip 44 is supported at a step portion 44a thereof which is in contact with the upper surface of the rack 41.

The operation of the embodiment will next be explained.

With the gripping body 2 gripped, the lower end portions of the eight cylinders 24 projecting downward from the multipipet 1 are simultaneously forced into eight nozzle tips 44 in one vertical row within the nozzle tip rack 41, thereby fitting nozzle tips 44 onto the respective lower end portions of the cylinders 24.

Since in the present invention the lower portion of each cylinder 24 is individually oscillatable by an amount corresponding to the gap l substantially around the portion sealed by the O-ring 26, when the eight cylinders 24 are simultaneously and respectively inserted into the nozzle tips 44, any small pitch error between the cylinders 24 and the nozzle tips 44 can be absorbed by the cylinders 24 which are capable of individually oscillating sidewardly in conformity with the pitch of the nozzle tips 44. Accordingly, all the nozzle tips 44 are properly fitted onto the lower end portions of the cylinders 24 and it is therefore unnecessary to make a manual check as to whether or not each nozzle tip 44 has been properly fitted or to correct the position of a nozzle tip 44 fitted improperly. Hence it is possible to improve the operational efficiency.

Next, the push button 5 of the multipipet 1 is pushed down against the spring 13 to cause the plunger unit 6 to move downward through the shaft 4, thereby simultaneously advancing the eight plungers 9 in the corresponding cylinders 24 by a predetermined stroke corresponding to a given amount of liquid to be sucked. In this state, the lower end portions of the right nozzle tips 44 are simultaneously inserted into eight corresponding sample filling holes of a microplate (not shown) and immersed in samples. The microplate is provided with a total of 96 holes filled with respective samples, the holes being arranged in 8 vertical rows and 12 horizontal rows at the same pitch as that of the bores 42a of the nozzle tip rack 41. The lower end portions of the above-described eight nozzle tips 44 are inserted into sample filling holes in a predetermined vertical row.

Next, the pressure applied to the push button 5 is removed. In consequence, the shaft 4 and the plungers 9 are returned to the positions shown in FIG. 3 by the action of the spring 13, thereby enabling a predetermined amount of a sample to be sucked into each nozzle tip 44.

Subsequently, the lower end portions of the eight nozzle tips 44 are simultaneously inserted into, for example eight holes (with no sample) of another similar microplate (not shown) and the push button 5 is pushed down. In consequence, the plungers 9 are moved downward through the same stroke as that in the above case, thus enabling the samples in the nozzle tips 44 to be discharged into the corresponding holes of another microplate. It should be noted that pipetting is not necessarily limited to an operation wherein samples are transferred from one microplate to another. For example, pipetting may be effected from a special-purpose container (reservoir) to a microplate or effected within a single microplate.

Since the multipipet 1 adopts the two-stage discharge system (for further details, refer to Japanese patent application No. 234512/1987), the push button 5 can be further pushed down. Thus, the samples left in the nozzles tips 44 after the first discharge operation can be completely discharged and there is therefor no difference between the amounts of sample sucked and discharged. Finally, the pressure applied to the push button 5 is removed. In consequence, the shaft 4 and the plungers 9 return to the positions shown in FIG. 3.

The operation of ejecting the nozzle tips 44 will next be explained. Referring to FIG. 5, as the push button 30 is pushed down against the spring 35, the ejector 33 moves downward together with the push button 30 as one unit. The lower surface of the ejector 33 first comes into contact with the upper ends of four outer nozzle tips 44, and pushes them down until these nozzle tips 44 are removed from the corresponding cylinders 24. As the push button 30 is pushed down further, the ceiling surface of the recess 33b subsequently comes into contact with the remaining four central nozzle tips 44 and removes then from the corresponding cylinders 24 in the same way. Since in this arrangement the nozzle tips 44 are removed in two stages, i.e., four at a time, the force required to eject the nozzle tips 44 is smaller than in the case where eight nozzle tips 44 are removed at a time. Thus, the operational efficiency is improved.

Figure 11:
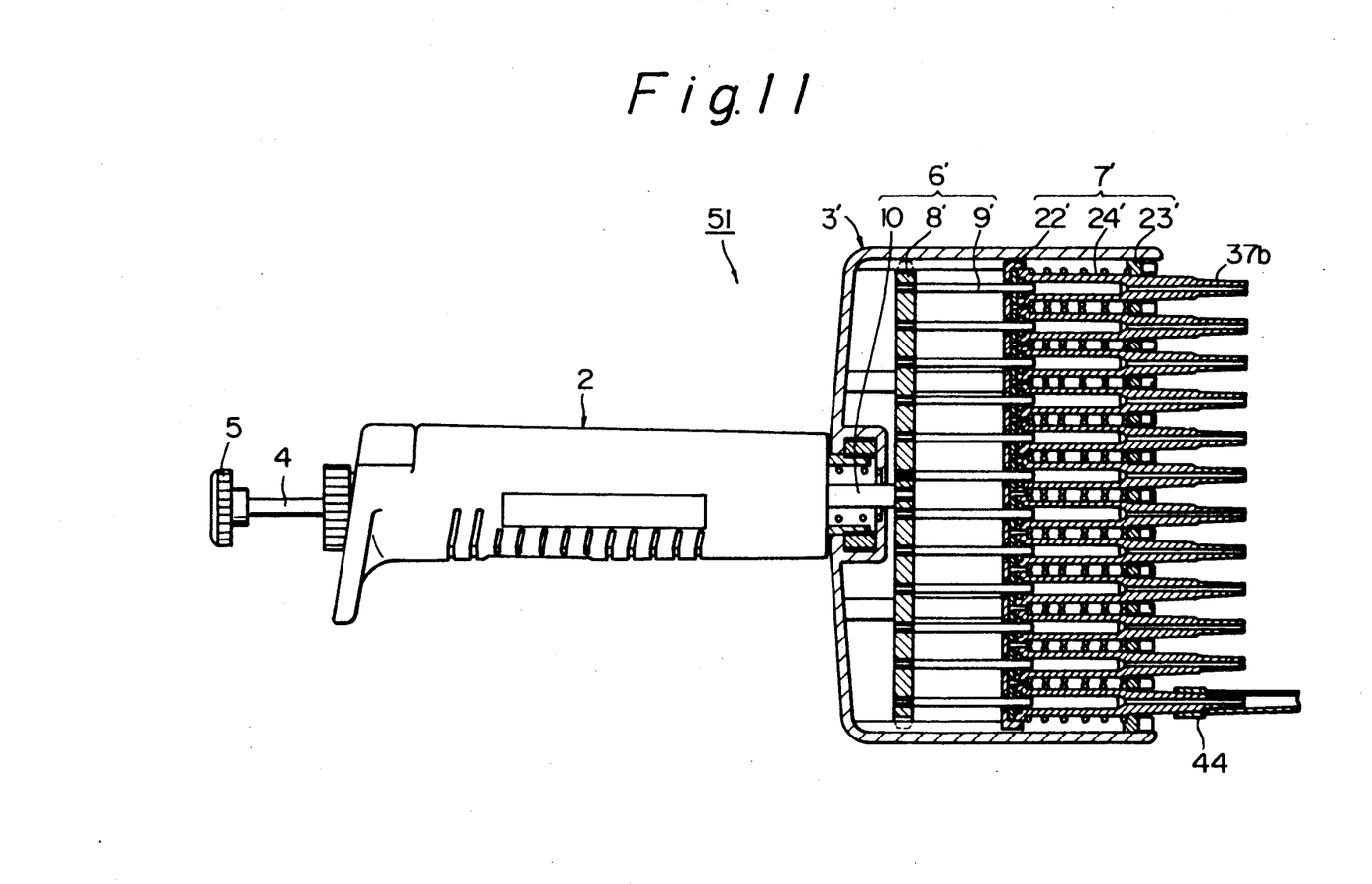
FIG. 11 is a partially sectioned front view of a 12-channel multipipet which is another embodiment of the multipipet according to the present invention.

FIG. 11 shows a 12-channel multipipet 51 which is another embodiment of the present invention. Description of those portions which are the same as those of the above-described 8-channel multipipet is omitted. Referring to FIG. 11, a cylinder unit 6' accommodated in a housing 3' has twelve plungers 9' attached to a common bar 8'. The cylinder unit 7' has twelve cylinders 24' retained between cylinder holders 22' and 23' in correspondence with the plungers 9'. The operation of the multipipet 51 is the same as that of the above-described embodiment except that nozzle tips 44 are fitted onto the respective lower ends of the twelve cylinders 24' and these nozzle tips 44 are simultaneously inserted into, for example, twelve sample filling holes in a horizontal row in the above-described first microplate. Then the samples thus sucked are simultaneously discharged into twelve holes of another microplate.

It should be noted that, unlike the cylinders 23 in the first embodiment, the cylinders 24' have extending portions 37b provided at the respective distal ends, as shown in FIG. 11. Therefore, when the nozzle tips 44 are attached to the corresponding cylinders 24', the extending portion 37b of each cylinder 24' enters the corresponding tip 44 to reduce the amount of air contained in the tip 44 by an amount corresponding to the volume of the extending portion 37b, thereby suppressing the influence of any error in volume which is likely to occur when a large amount of air is contained in the tip 44.

The multipipet of the present invention is, of course, applicable not only to 8- and 12-channel multipipets but also to those having various other numbers of channels.

What is claimed is:

1. In a multipipet designed to allow a plurality of plungers to be fittingly advanced by a manual operation in a plurality of cylinders, respectively, against the force of a spring, said plungers thereafter being returned to suck predetermined amounts of liquids into said cylinders and then moved downward again to discharge said predetermined amounts of liquids from said cylinders, an improvement characterized in that said cylinders are supported by a supporting member in such a manner that each cylinder is individually oscillatable sideward relative to said supporting member.

2. A multipipet according to claim 1, wherein each of said cylinders is supported by said supporting member at two portions thereof, that is, a first portion which is close to the corresponding plunger and a second portion which is remote from said plunger, in such a manner that each cylinder is supported at said first portion with a first radial gap with respect to said supporting member and at said second portion with a second radial gap with respect to said supporting member, thereby enabling each cylinder to oscillate sideward substantially around each of said first and second portions.

3. A multipipet according to claim 1, wherein said supporting member is a common and integral member which is used to mutually support all the cylinders.

4. A multipipet according to any one of claims 1, wherein each of said cylinders has a spring which biases the cylinder toward the corresponding plunger so that said cylinder abuts against a predetermined portion of said supporting member.

5. A multipipet according to claim 2, wherein said supporting member is a common and integral member which is used to mutually support all the cylinders.

6. A multipipet according to claim 2, wherein each of said cylinders has a spring which biases the cylinder toward the corresponding plunger so that said cylinder abuts against a predetermined portion of said supporting member.

7. A multipipet according to claim 3, wherein each of said cylinders has a spring which biases the cylinder toward the corresponding plunger so that said cylinder abuts against a predetermined portion of said supporting member.

* * * * *